US007283056B2

(12) United States Patent
Bukman et al.

(10) Patent No.: US 7,283,056 B2
(45) Date of Patent: Oct. 16, 2007

(54) METHOD AND COMPUTER PROGRAM FOR IDENTIFICATION OF INATTENTIVENESS BY THE DRIVER OF A VEHICLE

(75) Inventors: Elisabeth Bukman, Magstadt (DE); Lars Galley, Berlin (DE); Klaus-Peter Kuhn, Pluederhausen (DE); Dietmar Neumerkel, Berlin (DE)

(73) Assignee: DaimlerChrysler AG, Stuttgart (DE)

(*) Notice: Subject to any disclaimer, the term of this patent is extended or adjusted under 35 U.S.C. 154(b) by 366 days.

(21) Appl. No.: 10/996,040

(22) Filed: Nov. 24, 2004

(65) Prior Publication Data

US 2005/0128092 A1 Jun. 16, 2005

(30) Foreign Application Priority Data

Nov. 26, 2003 (DE) ................................ 103 55 221

(51) Int. Cl.
*G08B 23/00* (2006.01)

(52) U.S. Cl. ....................................... 340/575; 340/576

(58) Field of Classification Search .................... 701/1, 701/45, 301, 213, 117; 340/575–576, 425.5, 340/436

See application file for complete search history.

(56) References Cited

U.S. PATENT DOCUMENTS 4,611,199 A * 9/1986 Seko et al. ................. 340/576
5,745,031 A 4/1998 Yamamoto
6,061,610 A * 5/2000 Boer ............................. 701/1
6,405,132 B1 * 6/2002 Breed et al. ................ 701/301
2004/0088095 A1 * 5/2004 Eberle et al. ................. 701/45

FOREIGN PATENT DOCUMENTS

| | | |
|---|---|---|
| DE | 25 46 345 | 10/1975 |
| DE | 198 18 239 A1 | 4/1998 |
| EP | 0147539 | 7/1985 |
| JP | 60-76426 A | 4/1985 |
| JP | 04-274935 A | 9/1992 |
| JP | 7-093678 A | 4/1995 |
| JP | 2830475 B | 12/1998 |
| JP | 2001-273594 A | 10/2001 |
| JP | 2002-225586 A | 8/2002 |

OTHER PUBLICATIONS

Japanese Office Action dated Apr. 16, 2007 (Three (3) pages).

* cited by examiner

*Primary Examiner*—Jeffery Hofsass
*Assistant Examiner*—Shirley Lu
(74) *Attorney, Agent, or Firm*—Crowell & Moring LLP

(57) ABSTRACT

In a method and a computer program for identification when the driver of a vehicle is inattentive, a steering action following a steering quiescent phase is observed, in addition to the steering quiescent phase itself. The extent of the steering quiescent phase and of the steering action found are logically linked to one another, and the result of this logical operation is then used as a measure for the severity of the inattentiveness of the driver.

24 Claims, 6 Drawing Sheets

METHOD AND COMPUTER PROGRAM FOR IDENTIFICATION OF INATTENTIVENESS BY THE DRIVER OF A VEHICLE

BACKGROUND AND SUMMARY OF THE INVENTION

This application claims the priority of German patent document 103 55 221.9, filed Nov. 26, 2003, the disclosure of which is expressly incorporated by reference herein.

The invention relates to a method and apparatus, including a computer program, for determining when the driver of a vehicle (in particular a motor vehicle) is not paying attention during operation of the vehicle. The invention also relates to a computer readable storage medium encoded with such a computer program.

Various proposals have been made for detecting inattentiveness of a motor vehicle driver, including in particular a tendency for the motor vehicle driver to go to sleep. For example, German patent document DE 198 18 239 A1 discloses for this purpose an apparatus that comprises firstly a vehicle environment identification device for detection of the actual driving style of the motor vehicle driver, as well as a device for detecting a reference driving style (in particular, how many lateral self-movements there normally are by the motor vehicle driver in his driving style). Finally, the disclosed apparatus has comparison logic for comparing the reference driving style with the current actual driving style in order to output a warning to the motor vehicle driver based on the result of this comparison.

Furthermore, U.S. Pat. No. 6,061,610 discloses a method and apparatus for determining stress of the driver of a motor vehicle by detecting the steering wheel angle of the motor vehicle first of all in order to generate prediction errors for the steering wheel angle in the driver's control of the motor vehicle. A distribution of these prediction errors is then calculated and compared with another distribution of prediction errors of the steering wheel angle which represents a predetermined steering behavior of a stress-free or unstressed driver rather than the real steering behavior of the driver. The result of this comparison then represents the current stress on the driver while driving the motor vehicle.

German patent document DE 25 46 345 discloses a driver warning device for warning motor vehicle drivers before they go to sleep. The device detects the steering movement of the driver of the motor vehicle, on the assumption that, when the driver is awake, the steering wheel is not held entirely quiescent, even when traveling in a straight line; rather, steering movements are also still carried out continuously, even if they are very small. If the driver warning device detects absence of such steering movements over an adjustable time interval, as well, then the driver warning device deduces that the driver is going to sleep or is at least at risk of going to sleep, and warns him or her by outputting a signal.

The driver warning device disclosed in the German patent document DE 25 46 345 has the disadvantage that the decision on when the driver of a vehicle is not paying attention is made solely on the basis of the detection of a steering quiescent phase; thus, this decision can be made only vaguely and unreliably.

Japanese patent document JP 07-093678 A describes an apparatus for identification of fatigue by identification of a steering quiescent phase with subsequent identification of a corrective steering action.

Against the background of this prior art, one object of the present invention is to provide a method and apparatus (including a corresponding computer program) to identify when the driver of a motor vehicle is not paying attention, as well as a controller for carrying out this method and a data storage medium encoded with such a computer program, which make it possible to identify more reliably identify possible inattentiveness of the driver.

This and other objects and advantages are achieved by the method according to the invention, which includes the following steps: identification of a steering action following a steering quiescent phase; determination of the magnitude of the extent of this steering action by evaluation of the rate of change of the steering wheel angle; and determination of a measure of the severity of the inattentiveness by the driver by assessment of the result of a link between the extent of the steering quiescent phase and the extent of the steering action.

In the process of identification of inattentiveness of the driver, the invention advantageously distinguishes between a steering quiescent phase and a more or less hectic steering action which typically follows a state of inattentiveness. Thus, according to the invention, a state of inattentiveness is not assumed unless both the steering quiescent phase and the subsequent steering action are identified in conjunction with one another. Conversely, this means that identification of a steering quiescent phase or of a steering action by itself is not sufficient to deduce inattentiveness of the driver. The detected extents of both the quiescent phase and of the steering action are logically linked to one another for determination of the extent of the severity of the inattentiveness, and the result is then assessed.

In modern vehicles, in particular motor vehicles, a sensor for detection of the steering wheel angle x is normally provided in any case. Thus, in principle, no additional sensors are advantageously required to implement the described method.

Two different representative embodiments for implementation of the invention will be explained in the description. In principle, a specific way to determine the extent of the steering quiescent phase is provided in the second exemplary embodiment; however, this determination process can also be carried out according to the first exemplary embodiment.

ADVANTAGES OF THE FIRST EXEMPLARY EMBODIMENT

Calculation of the extent of the steering action solely by formation of a steering wheel angle variance would merely represent the instantaneous steering behavior of the driver. However, in order to make a reliable determination regarding inattentiveness, it is in fact important to take account of changes in the steering behavior over time, as well. According to the invention, this aspect is taken into account by including two steering wheel angle variances in the formation of the variance ratio, which variances represent the steering action of the driver at different times that are offset by a time interval $\Delta t$ relative to one another.

The variance ratio calculated according to the invention can intrinsically advantageously be interpreted as a measure of the severity of the inattentiveness of the driver while steering the vehicle at the time t1; inattentiveness of the driver exists in particular when this variance ratio has a value greater than 1.

ADVANTAGES OF THE SECOND EXEMPLARY EMBODIMENT

In contrast to the first exemplary embodiment, the second exemplary embodiment makes use of considerably fewer parameters for assessment of the inattentiveness of the driver. It is therefore less memory intensive. Furthermore, due to the use of considerably simpler algorithms, it can be dealt with more easily and can be implemented in real time. Overall, it is therefore highly suitable for practical use in a vehicle.

It is thus advantageous that an assessment of the extent of the steering quiescent phase (that is, its time duration) is made only by evaluation of the steering wheel angle; and the extent of the steering action is preferably determined only by detection of the maximum steering angle wheel gradient that occurs. There is therefore no need for any calculation or evaluation based on the variance function.

Logically linking the extent of the steering quiescent phase to the extent of the steering action in order to determine a measure for the severity of the inattentiveness by the driver is carried out in the second exemplary embodiment by means of a multidimensional operator. In order to save unnecessary computation complexity, however, the logical operation is preferably carried out only when both the steering quiescent phase and the expected subsequent steering action each take place with a predetermined minimum extent. If the steering quiescent phase or the steering action are not sufficiently sharply pronounced, then, according to the invention, it is assumed that the driver is not in a state of inattentiveness.

ADVANTAGES COMMON TO BOTH EXEMPLARY EMBODIMENTS

The result of the logical operation from either the first or second exemplary embodiment (that is, the variance ratio or the result of the operator logical operation) can advantageously be mapped onto a probability value with the aid of the sigmoid function. This means that it is possible to specify a probability (between 0 and 100%) of the driver having been inattentive in the steering of the vehicle at the time t1.

In a further advantageous refinement, the claimed method based on the previously determined probability value allows a statement to be made regarding the probability with which the behavior of the driver can be associated with one specific fatigue level which is suitably selected and is predetermined from a large number of such levels. According to the invention, such an association is always made taking into account the currently detected steering wheel angle.

This association with the predetermined fatigue levels can advantageously be made more precise by taking into account not only the steering wheel angle as a first indicator but also further observable indicators for the inattentiveness by the driver, such as his eyelid closure behavior or his reaction time.

It is also advantageous that the estimate of the fatigue of the driver can also be made more precise by taking into account not only the currently detected values of, in particular, the stated indicators, but also the fatigue classifications carried out in the recent past. In other words, this procedure allows a plausibility check of the new estimate, taking into account the fact that the driver fatigue is not a phenomenon which occurs or disappears again suddenly, but which in fact changes only continuously over the course of time.

Not only does the claimed method advantageously allow a conclusion to be drawn about driver fatigue as the cause of the detected inattentiveness, as described above, but it also allows a conclusion to be drawn relating to other causes for the detected inattentiveness (for example, a conversation being held with a front seat passenger or the operation of an apparatus, such as the radio or the glove compartment in the vehicle).

In order to improve the reliability of a statement regarding the attention level or inattentiveness of the vehicle driver, it is worthwhile to evaluate not only a result of the logical operation according to the first or second exemplary embodiment but, as an alternative, to base this statement on a large number of such logical operation results. In this case, this plurality may comprise not only mere results from the first or from the second exemplary embodiment, but also a mixture of results from the first and second exemplary embodiments. Specifically, a statement can be made more reliably about the inattentiveness by the driver by weighting each result obtained from a logical operation with an associated weighting factor in order to obtain an averaged logical operation result in the final analysis from the present plurality of weighted logical operation results, by mathematical averaging. This averaged logical operation result then represents a more reliable measure of the degree of the inattentiveness by the driver in the steering of the vehicle at a specific time, than does a non-averaged logical operation result.

Finally, it is advantageous, in particular, for the driver of the vehicle to be informed of the identified inattentiveness in the form of visual or audible warning information.

The object of the invention as mentioned above is also achieved by a computer program for carrying out the described method, by a data storage medium encoded with the computer program, and by a controller programmed to carry out the described method.

This computer advantageously need be programmed only once at least for individual vehicle types, and can then be implemented in all the vehicles of a corresponding model.

DETAILED DESCRIPTION OF THE DRAWINGS

Figure 1:
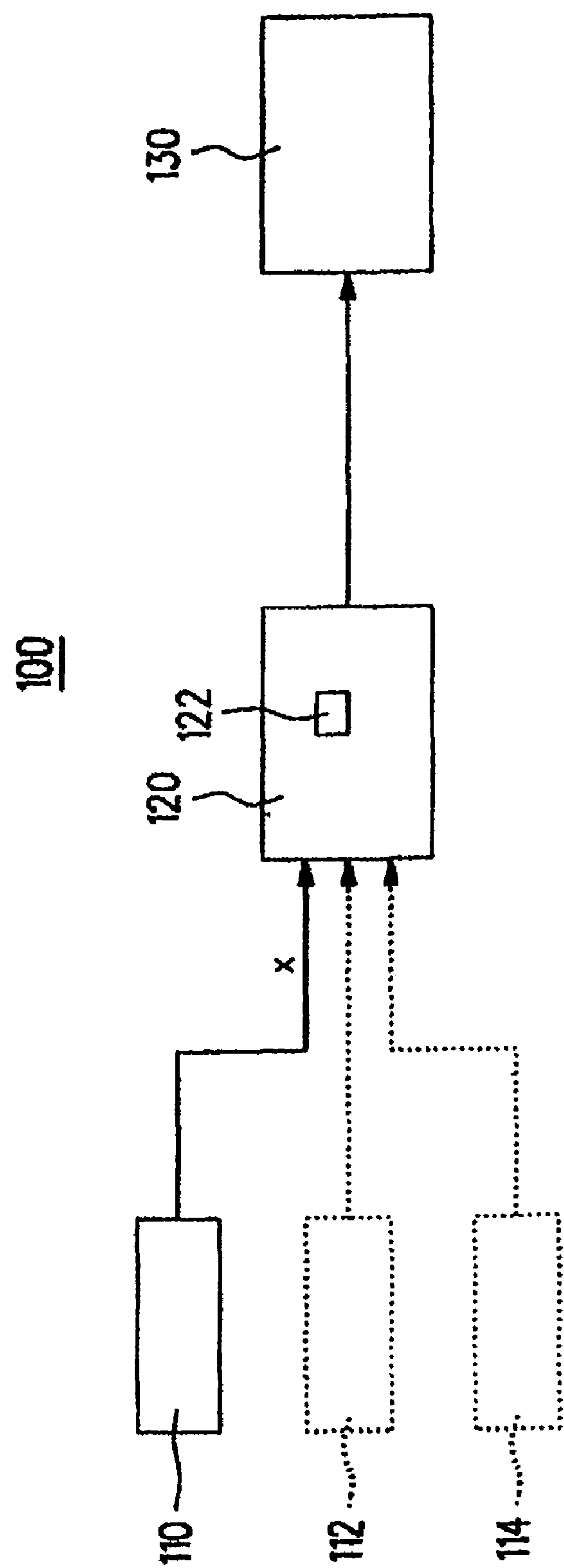
FIG. 1 shows a controller for implementing the method according to the invention.

FIG. 1 shows a controller 100 for carrying out the method according to the invention for identifying inattentiveness by the driver of a vehicle, in particular of a motor vehicle. The controller is preferably mounted in the vehicle (not shown) and comprises a steering wheel angle sensor 110 for detection of the current steering wheel angle x (that is, the steering movement) caused by the driver. A control device 120 (preferably in the form of a microcontroller) detects a sensor signal which is produced by the steering wheel angle sensor 110 and represents the steering wheel angle x.

The steering wheel angle x represents a first indicator, which is preferred according to the invention, of inattentiveness by the driver. In addition to the steering wheel angle, the control device 120 can also in principle receive and evaluate further sensor signals from other sensors 112, 114 as further indicators of the inattentiveness by the driver. Such further sensor signals will be ignored initially, but are mentioned further below in the description.

Inattentiveness by the driver is identified by running a computer program 122 in the control device 120, using a method according to the invention and described in the following text, by evaluating the steering wheel angle x as a preferred indicator. If driver inattentiveness is found, it is advantageous for the control device 120 to drive a warning device 130 to emit audible or visual warning information to the driver. The warning information makes the driver aware of his inattentive behavior in driving of the vehicle, and provides him with the opportunity to re-establish his attention.

Figure 2:
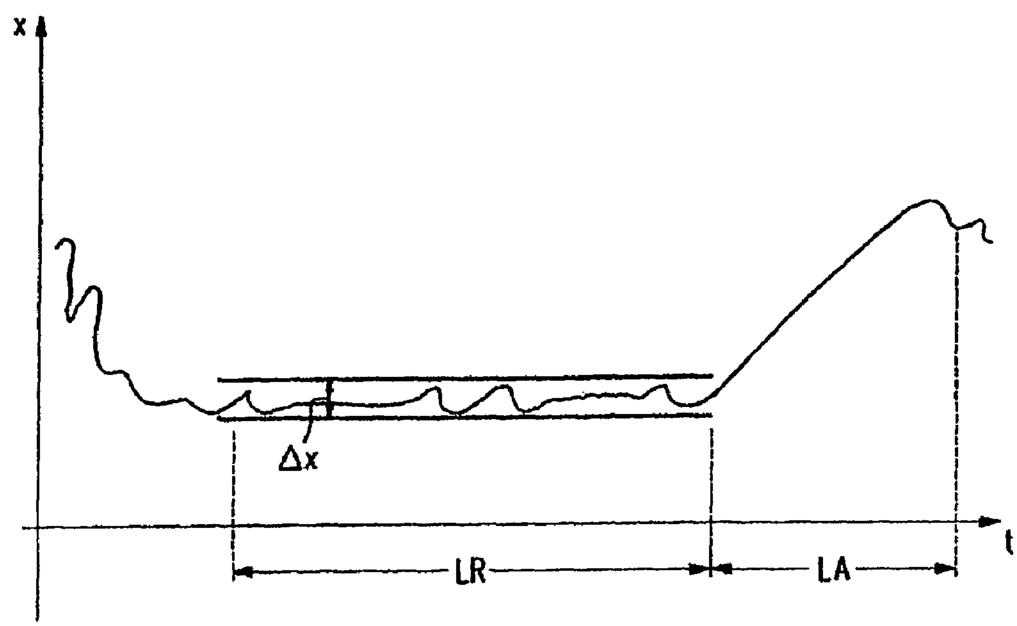
FIG. 2 shows an example of the profile of the steering angle x when driver inattentiveness occurs, according to the invention.

FIG. 2 shows a typical profile of the steering wheel angle, such as occurs when inattentiveness by the driver has been identified with the aid of the present invention. In this profile, first of all, the driver has a steering quiescent phase LR in which he makes no significant changes. Thus, in FIG. 2, the steering angle x remains in the deflection range Ax, which is bounded by the two parallel horizontal lines, throughout the steering quiescent phase LR. The occurrence of inattentiveness in the sense of the invention is then characterized by a very sharp or powerfiil steering action which follows this steering quiescent phase. This powerful steering action LA is represented in FIG. 2 by the rapid rise in the steering angle x at the end of the quiescent phase.

Figure 3A:
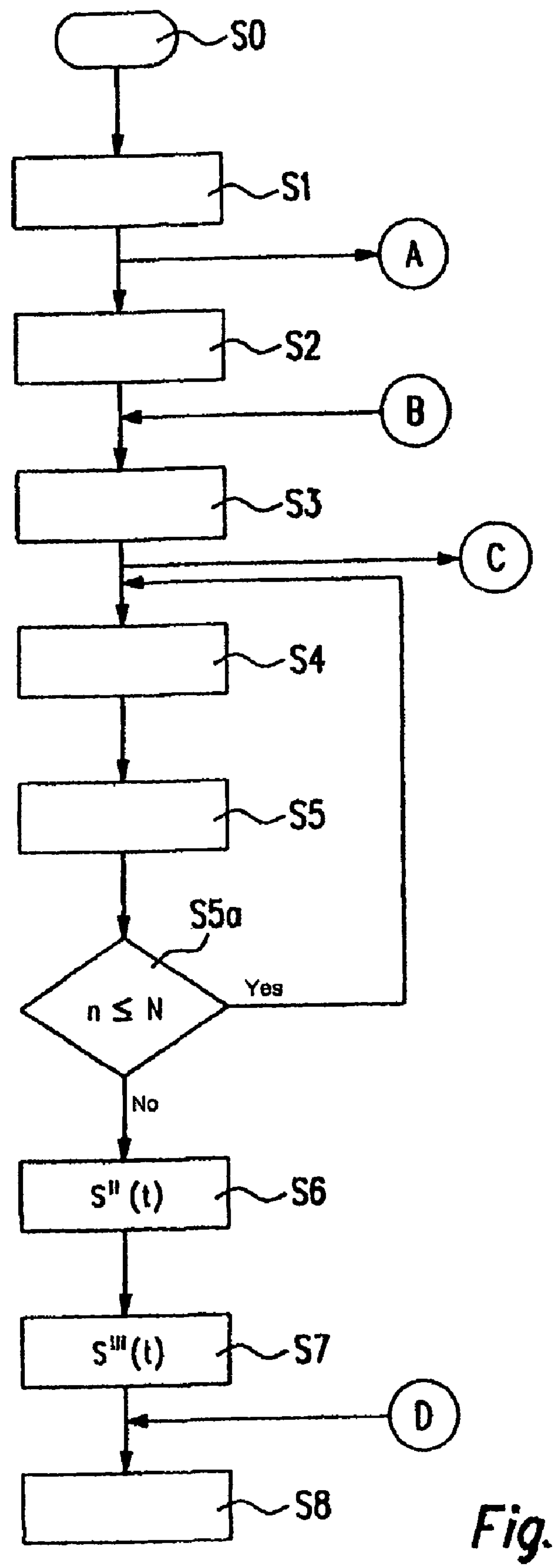
FIG. 3*a* is a flow diagram that depicts the procedure for the method according to the invention based on a first exemplary embodiment.
Figure 3B:
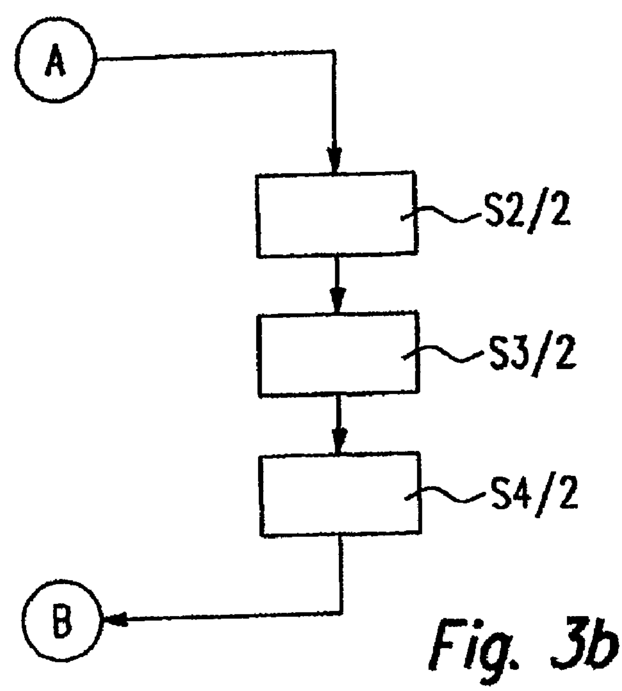
FIGS. 3*b, c* in conjunction with FIG. 3*a* show the procedure for the method according to the invention based on a second exemplary embodiment.

FIG. 3 shows the method according to the invention, implemented with the aid of the controller 100 described above. Steps S0-S8 shown in FIG. 3*a* first of all represent a first exemplary embodiment of this method. (The branches A, B, C and D shown in FIG. 3*a* are irrelevant to this first exemplary embodiment; they will not become relevant until the description of a second exemplary embodiment of the method according to the invention, which follows the description of the first exemplary embodiment.)

First Exemplary Embodiment

Following a starting step S0, the first exemplary embodiment as shown in FIG. 3*a* provides for the detection of a steering movement of the steering wheel of the vehicle (that is, the detection of the steering behavior of the driver) in the form of the steering wheel angle x (method step S1). The steering quiescent phase LR, see FIG. 2, is then identified in a second step S2 on the basis of the detected steering wheel angle x. A variance ratio w (x, t1) is then likewise calculated in step 2, as the quotient of a second steering wheel angle variance divided by a first steering wheel angle variance. In this case, the first steering wheel angle variance v(x, t1−Δt) at an early time t1−Δt is calculated using the following formula (1):

$$v(x, t_1 - \Delta t) = \mathrm{var}(x(t_1 - \Delta t), \ldots, x(t_1 - \Delta t - T)) = \frac{1}{T}\sum_{t=(t_1-\Delta t)}^{(t_1-\Delta t-T)} (x(t) - \overline{x})^2 \quad (1)$$

where:

$x(t_1-\Delta t)$ represents the steering wheel angle x at the time $t_2-\Delta t$;

Δt represents a multiple of the sampling interval;

T represents an observation time window;

$t_1-\Delta t$ represents the observation time;

$\overline{x}$ represents a time mean value of the steering wheel angle x averaged over the observation time window T; and var represents the mathematical variance function.

The second steering wheel angle variance $v(x, t_1)$ is calculated using the following formula (2):

$$v(x, t_1) = \mathrm{var}(x(t_1), \ldots, x(t_1 - T)) = \frac{1}{T}\sum_{t=(t_1)}^{(t_1-T)} (x(t) - \overline{x})^2 \quad (2)$$

where the variables have the same meanings as in the formula (1) with the only difference being that they are considered at the observation time $t_1$.

The variance ratio vv(x,t1) is then calculated from the first and second steering wheel angle variances as follows:

$$vv(x, t_1) = \frac{x(x, t_1)}{v(x, t_1 - \Delta t)}. \quad (3)$$

The variance ratio calculated in the method step S2 therefore represents a reliable measure of the degree of inattentiveness of the driver in steering of the vehicle at the time t1, because it effectively records the typical steering behavior of a driver when he is not paying attention. As noted previously, and shown in FIG. 2, such behavior is characterized by a first steering quiescent phase LR without any steering activity, or with only a minor amount of steering activity, followed by a second steering action phase LA with above-average powerful steering movements. The first phase leads, at the early observation time t1−Δt, to the first variance at a small magnitude. In contrast, the second phase, in particular at the time t1, leads to a considerably greater value for the second variance. Overall, this results in a small value for the denominator and a large value for the numerator, so that, overall, these two effects result in a high value for the variance ratio. As long as the variance ratio is ≦1, this indicates that the driver is not inattentive. Only when the variance ratio assumes a value greater than 1 does this indicate that the driver of the vehicle is not paying sufficient attention to the road traffic.

Figure 4:
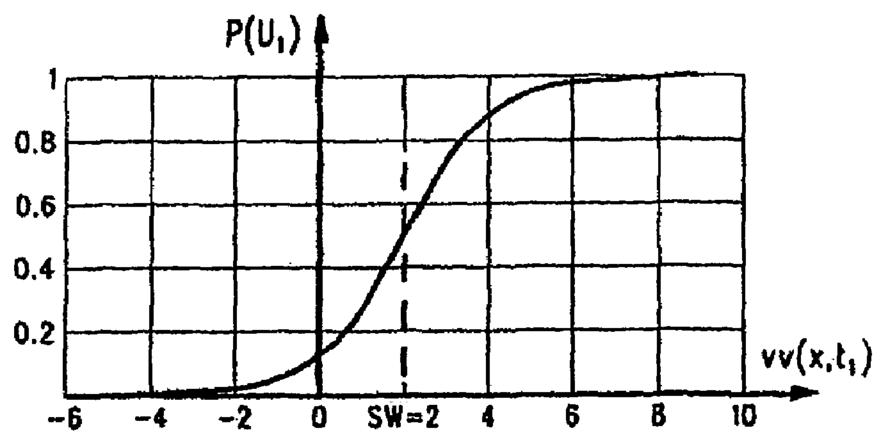
FIG. 4 illustrates a sigmoid function.

The value of the variance ratio may in theory be indefinitely high. However, indefinitely high values are unsuitable to allow the inattentiveness of the driver to be classified sufficiently accurately. Accordingly, in one particular variant of the method according to the invention, the variance ratio is converted to a probability value in a subsequent method step S3. This conversion is preferably carried out with the aid of a sigmoid function, which is illustrated in FIG. 4 and has a suitable predetermined threshold value SW. This threshold value for the sigmoid function illustrated in FIG. 4 is SW=2. This means that a variance ratio vv(x, t1) (which is plotted on the abscissa in FIG. 4) of 2 indicates a probability P(Un), where n=1 (first indicator), of 0.5 (that is, 50%) that the driver of the vehicle has become inattentive at the time t1. As can be seen from the graph of the sigmoid function in FIG. 4, the probability P(U1) may in principle assume a value between 0 and 100%, depending on the magnitude of the variance ratio.

The sigmoid function ensures a "soft" transition from total attention (corresponding to a probability value for the instantaneous inattentiveness of 0) to total inattention (corresponding to a value for the inattentiveness of 1=100%). Mathematically, the sigmoid function illustrated in FIG. 3 is calculated using the following formula (4):

$$P(U_1) = \frac{1}{1 + e^{-(vv(x,t_1)-S)}}, \tag{4}$$

where $P(U_1)$ represents the probability of the inattentiveness by the driver in steering of the vehicle, with $U_1$ representing an inattentiveness event detected with the aid of the first indicator (steering wheel angle: n=1), and S representing the threshold value.

The evaluations of the steering wheel angle x carried out so far (that is, up to and including the method step S3) have allowed identification of the presence or absence of inattentiveness by the driver at the time t1. A further evaluation of the knowledge obtained up to this point, preferably with the aid of a dynamic probabilistic model, further allows conclusions to be drawn regarding the possible causes of inattentiveness that has been found. The method steps S4-S6, which are described in the following text, therefore indicate a method by which it is possible, for example, to determine the probability that fatigue is the cause of the detected driver inattentiveness.

Figure 5:
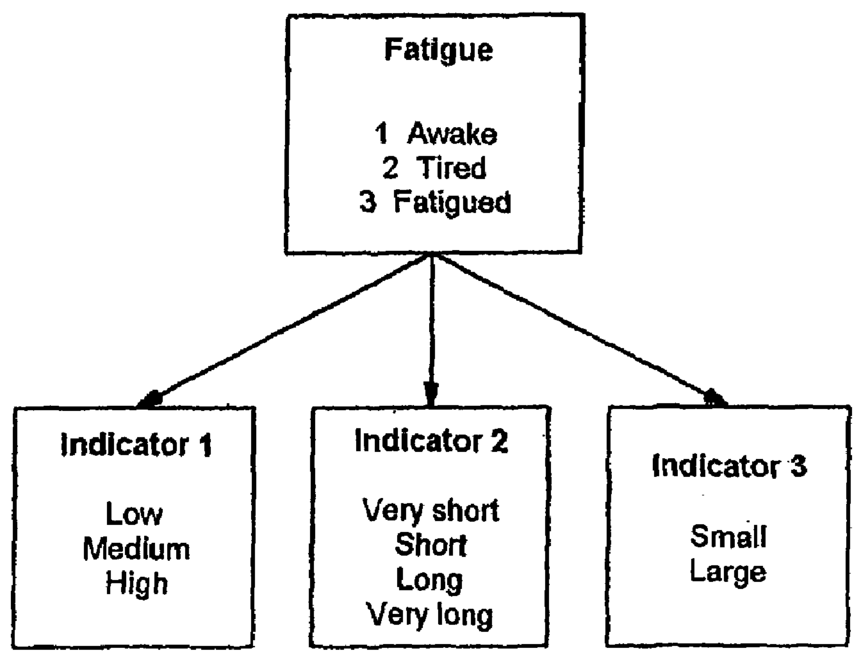
FIG. 5 is a first cause and effect diagram.

This relationship which has just been described (between fatigue as the cause of inattentiveness in the steering of the vehicle) is illustrated in FIG. 5. The arrows shown there point from fatigue as the cause to various possible effects, in particular to inattentiveness in the steering of the vehicle (indicator 1). In addition, however, fatigue may also have other observable effects, such as frequent closure of the eyelids (indicator 2) or a delayed reaction capability (indicator 3).

According to the invention, in order to deduce the occurrence of driver fatigue from a detected inattentiveness event in the steering of the vehicle, a first probability vector On=1 is determined in method step S4. The elements $O_{n=1,\ kn=1}$ each represent values of the probability value P(U1) occurring in individual, predetermined and suitably selected extent levels $k_n$, where $k_n \epsilon \{1 \ldots K\}$. The parameter n in this case represents an evaluated indicator, with n=1 representing the steering behavior or the steering wheel angle as an indicator.

Figure 6:
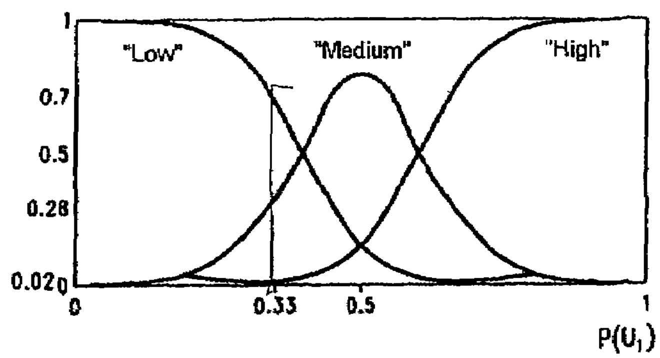
FIG. 6 shows Gaussian distributions for various extent levels in which a probability value which represents driver inattentiveness may occur.

In FIG. 6, which the process for determining the first probability vector $O_{n=1}$ the probability value $P(U_1)$ (representing the probability of inattentiveness by the driver in steering of the vehicle at the time $t_1$ as determined in the previous method step S3) is plotted between 0 and 100% on the abscissa. The previously determined probability value $P(U_1)$ will now be predetermined in the method step S4, and associated with suitable defined extent levels $k_n \epsilon \{1 \ldots K_1\}$. In the exemplary embodiment shown in FIG. 6, three extent levels were predetermined, "low" ($k_1$=1), "medium" ($k_1$=2) and "high" ($k_1$=3) (FIG. 5) for indicator 1, and each represented by their own Gaussian function in FIG. 6. The number of extent levels for the indicator 1 in this example is thus $k_1$=3.

The number and parameters of these Gaussian functions for the respective extent levels, such as their center points or their variances, can be configured appropriately depending on the application. As can be seen from FIG. 6, a probability of 70% of this probability value occurring with only a small extent would be associated, after carrying out the method step S4, with a probability value $P(U_1)$ (assumed by way of example) of 0.33 for the inattentiveness by the driver. There is a 28% probability of the calculated probability value occurring with a medium extent, while there is a probability of only 2% of the calculated probability value occurring with a high extent.

In other words, in the case of the example illustrated in FIG. 6 (an assumed probability value of 0.33 for the inattentiveness by the driver at the time $t_1$), it can be concluded that there is a 70% probability that the extent of inattentiveness by the driver is low. (That is, there was a 70% probability that the driver was paying attention.) This also results in the statement that there was a probability of 28% that the driver was paying medium attention, and that there was a probability of only 2% of his being highly inattentive.

An indefinite number of fatigue levels can now be defined in the next method step S5, and conditional probabilities between these levels as well as the observed steering inattentiveness event can now be allocated. In the example shown in FIG. 5, three fatigue levels ("awake", "tired" and "fatigued") are provided. Conditional probabilities can then likewise be allocated, also in the method step S5, in the form of a matrix B between each of these fatigue levels and one of the extent levels described above. This matrix B covers a total number of matrix elements which is calculated from the product of the number of extent levels multiplied by the number of predetermined fatigue levels. If there are three extent levels "low", "medium" and "high" for the steering inattentiveness event, the three fatigue levels mentioned above result in a total number of 3*3=9 conditional probabilities for the matrix B. By way of example, one of these indicates the probability of a steering inattentiveness event in the "high" extent level occurring, given that the probabilistic model in the first fatigue level is "awake". These conditional probabilities can be configured appropriately.

With the probability vector $O_{n=1}$ as determined in step S5, and the calculated matrix B, it is possible to determine, in a method step S6, a fatigue probability vector S', whose elements each represent probabilities P (fatigue level) that the detected degree of inattentiveness by the driver in steering of the vehicle is associated with individual, predetermined and suitably selected fatigue levels. The fatigue probability vector S' is calculated using the following formula (5):

$$S'(t)=O_1^T \cdot B_1 \tag{5},$$

where $O_{n=1}^T$ represents the transpose of the first probability vector; and $B_1$ represents the matrix B for the detected indicator for steering inattentiveness, represented by the index 1.

The calculation rule (5) just described for calculation of the fatigue probability vector S' has the disadvantage that it is based only on an evaluation of the steering wheel angle x as an indicator (n=1). Other possible observable effects of fatigue, such as those indicated in FIG. 5 by the indicators 2 (for example eyelid closure frequency) or the indicator 3 (for example reaction time) are not included in the formula 5 for calculation of the fatigue probability vector.

However, it is also possible to use these indicators 2 and 3 as well as further suitable indicators n (for example the yaw angle of the vehicle, the distance from the vehicle in front or the leaving of a lane, to the extent that these can be measured) to calculate a more precise fatigue probability vector S". The method steps S4 and S5 which have just been described must then be carried out separately in each case not only for the observed steering angle as the indicator n=1, but also for further desired indicators such as the eyelid closure behavior (n=2) and/or reaction time (n=3), etc. (method step S5a).

In the course of method step S4, an individual number of extent levels $k_n$ where $k_n=1 \ldots K$ must then be defined individually for each indicator n. This number of extent levels $k_n$ then corresponds in each case to the number of elements in a probability vector $O_n$ associated with the respective indicator. These elements $O_{n\_kn}$ in each case represent probabilities $P(O_{n\_kn})$ of probability values $P(U_n)$ for the other inattentiveness indicators (n=2 . . . N) occurring in addition to the steering inattentiveness (n=1) in the individual extent levels $k_n$ which are predetermined and suitably selected individually for the indicators.

A corresponding matrix Bn can then also be predetermined individually for these further indicators n, corresponding to the method step S5, once again. The more precise fatigue probability vector S" is then calculated on the basis of the data that is then available in step S6, using the following formula (6):

$$S''(t) = \prod_{n=1}^{N} O_n^T \cdot B_n, \tag{6}$$

where:

- n represents the n-th indicator for the inattentiveness by the driver,
- $k_n$ represents the k-th element of the vector $O_n$ or the k-th extent level for the indicator n;
- $O_n^T$ represents the transpose of a probability vector;
- $B_n$ represents the matrix of conditional probabilities between individual predetermined fatigue levels and an inattentiveness event which is indicated by the indicator n; and
- N represents the number of indicators used.

In the two variants which have been described so far for calculation of the fatigue probability vector S, only the extent of a detected inattentiveness event has been traced back to the most probable actual fatigue level, be this on the basis of a detected steering inattentiveness event, on the basis of additionally detected events (such as increased eyelid closure behavior or shortened reaction time). Further details of this process of tracing back from the observed inattentiveness to an existing fatigue level as the cause thereof can be achieved by taking account not only of the severity of the inattentiveness event but also the most probable fatigue level determined in a previous time interval. This ensures that once an inattentiveness event has been detected, or has been detected for the first time, it does not in itself lead immediately to the conclusion that the fatigue level is high. This would not be consistent with the actual characteristic of fatigue since, in principle, fatigue is a phenomenon which does not occur suddenly, but builds up slowly only over the course of a period of time.

In the case of the three fatigue levels mentioned above and described in FIG. 5, the change from one fatigue level to another is therefore provided with different conditional probabilities. These conditional probabilities are preferably predetermined in a suitable manner in the form of a matrix A in the course of the probabilistic model. The conditional probabilities in the matrix A are intended, in particular, to express the fact that, for example, a direct transition from fatigue level 1"awake" to fatigue level 3, "fatigued" is considerably less probable than a direct transition from level 1 to level 2, "tired", in which, in comparison to level 1, initial adverse effects in terms of the attention of the driver can now be identified. The configuration of the matrix A should also take account of the fact that the transitions from being awake to a state of greater fatigue take place with different conditional probabilities, in the same way as the transitions from a fatigued state to being awake.

With the most probable fatigue level determined in a previous time period also being taken into account, the fatigue probability vector S''', whose precision has been further enhanced in this way, is then calculated in step S7 using the following recursive formula (7):

$$S'''(t_1)=S''(t_1)\cdot A\cdot S'''(t_1-1) \tag{7},$$

where

- $S''(t_1)$ represents the more precise fatigue vector S" without consideration of the most probable fatigue level determined in the previous time interval;
- A represents the matrix of conditional probabilities between a fatigue level in the most recent time interval and a current fatigue level; and
- $S'''(t_1-1)$ represents the more precise fatigue vector S''' in the time period $t_1-1$.

It is recommended that an initial value of $S'''(0)=(1, 0, 0)^T$ be used as the third variant in order to start the recursive calculation of the more precise fatigue probability vector S''' using the formula (7).

In other words, the more precise calculation of the fatigue probability vector S''' using the formula (7) smoothes the fatigue vector over time, and/or prevents an inattentiveness event which has been identified for the first time from leading immediately to a sudden change in the fatigue level which is assumed to be the most probable cause of the detected inattentiveness event. Suitable configuration of the matrix A, in particular, also ensures that, conversely, a high degree of attention by the driver, which is detected suddenly, does not immediately lead to a low fatigue level if a very high fatigue level has been determined to be the probable cause of an immediately preceding detected inattentiveness.

Figure 7:
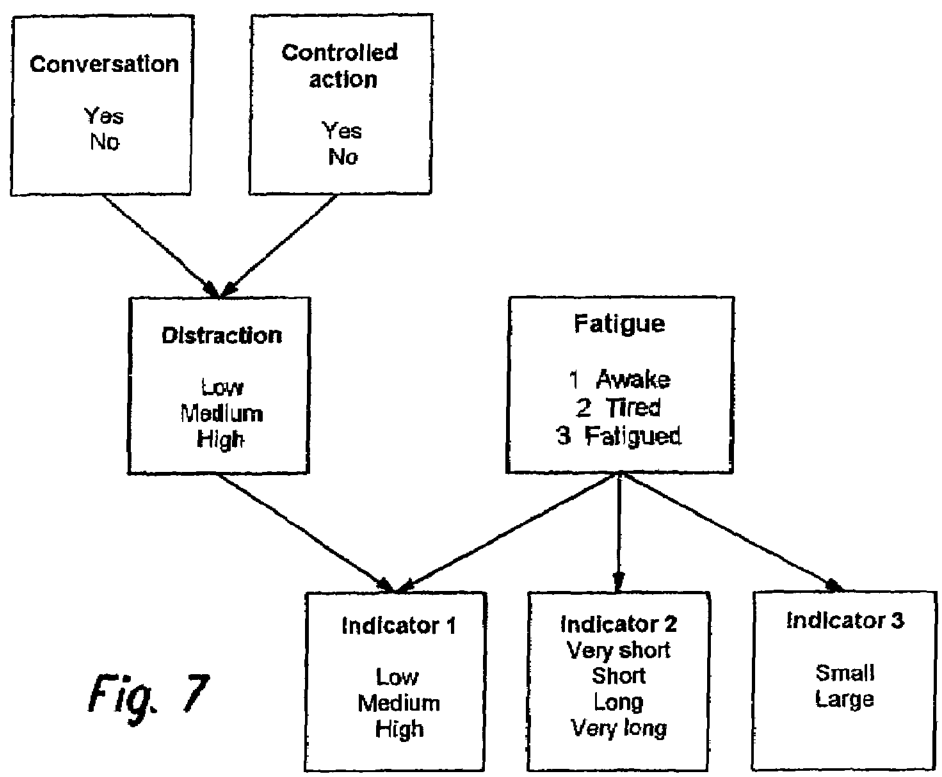
FIG. 7 is a second cause and effect diagram.

The method described thus far has always had the aim of deducing a certain fatigue level as the cause of the detected inattentiveness, based on detected steering inattentiveness (and, optionally, also on the basis of further indicators for driver inattentiveness). This is illustrated once again in graphic form in FIG. 7, where the arrows point from a cause to an effect. However, the directions of the arrows in FIG. 7 also show that, according to the model on which this is based, the fatigue is immediately the sole cause for the indicators 2 (eyelid closing behavior), and 3 (shortened reaction time), but that this need not be the only cause of detected steering inattentiveness. In fact, in addition to or as an alternative to fatigue, a given temporary distraction of the driver may also be the cause of detected driver steering inattentiveness. The reason for distraction may in turn be, for example, a conversation being held with the front seat passenger or an action carried out on a control element, such as the radio or the glove compartment in the vehicle. If, in addition to the previously mentioned inattentiveness events or indicators, possible causes for distraction are also additionally detected with the aid of suitable sensors, such as a microphone 112 or a camera 114 (see FIG. 1), then latter events can be evaluated with the aid of the probabilistic model in order to make a statement about the probability with which it can be assumed that the driver has been distracted, for example owing to a conversation being held or a control action being carried out, and the probability of fatigue being the cause of the observed inattentiveness.

The driver inattentiveness which is detected by one of the variants of the first exemplary embodiment is finally compared with an error criterion, in particular with a respectively suitably predetermined threshold value, in order then to output a warning signal to the driver on the basis of the result of this comparison (method step S8 as shown in FIG. 3*a*).

Second Exemplary Embodiment

The second exemplary embodiment of the method according to the invention is in principle independent of the first exemplary embodiment, but shares individual method steps which are identical to the individual method steps from the first exemplary embodiment. One fundamental difference between the first and the second exemplary embodiment is that, in the first exemplary embodiment, the identification of a steering action LA and the calculation of a logical operation result between the extent of the steering quiescent phase and the extent of the steering action coincide in the form of the calculation of the variance ratio. In contrast, the second exemplary embodiment offers the advantage that not only the steering quiescent phase LR but also the subsequent steering action LA and the logical linking according to the invention of the extents of these two phases can be carried out in each case separately (as separate method steps), as will be described in more detail in the following text with reference to FIGS. 3*a*, 3*b* and 3*c*.

After a starting step S0, the second exemplary embodiment as shown in FIG. 3*a* first of all provides for the detection of the steering movement of the steering wheel of the vehicle (that is, the steering behavior of the driver in the form of the steering wheel angle x) in method step S1. To this extent, the first and the second exemplary embodiment still coincide. For the second exemplary embodiment, however, this is not followed by the method step S2 as shown in FIG. 3*a*; rather, the method branches via the mark A to FIG. 3*b*, while the extent (time duration) of the steering quiescent phase is first of all determined in the method step S2/2. A steering quiescent phase exists for as long as the steering angle of the vehicle is within a predetermined steering wheel angle interval Ax. (See FIG. 2.) The time period for which this situation lasts then represents the extent of the steering quiescent phase LR.

The extent of a steering action following the detected steering quiescent phase is then detected in a method step S3/2. The maximum gradient of the steering angle which then occurs is determined for this purpose. In FIG. 2, this gradient is illustrated in the form of the gradient of the steering angle, how it occurs, once the steering wheel angle has left the steering wheel angle interval Ax.

The extent of the steering quiescent phase and of the steering action are then linked to one another in the method step S4/2 by means of a multidimensional operator (which may be a family of characteristics, a weighting function or a logical decision function). The result of this use of the multidimensional operator then represents a suitable measure for the severity of the inattentiveness of the driver in steering of the vehicle. The logical linking of the two extents which have been mentioned is, however, preferably carried out only when it has been found in the prior steps S2/2 or S3/2 that the extent (time duration) of the steering quiescent phase exceeds a predetermined minimum time period, and the maximum gradient of the steering wheel angle is greater than a predetermined gradient threshold value. Otherwise, the extents of the steering quiescent phase and of the steering action are not regarded by the method according to the invention as being sufficiently pronounced to allow the deduction of driver inattentiveness as a result of their combined presence.

The multidimensional operator is preferably dimensioned on the basis of the current speed of the vehicle and/or on the basis of the dynamics of the driving style of the driver. Specifically, this means that the evaluation of the detected extents of the steering quiescent phase and of the steering action take account of the fact that the steering movements are typically less at high vehicle speeds than at low speeds. Matching to the driving style of the driver prevents a hectic steering movement which is carried out deliberately, for example by a rally driver, in conjunction with a previously detected supposed steering quiescent phase from being interpreted incorrectly as driver inattentiveness.

The logical operation result determined in method step S4/2 according to the second exemplary embodiment can now be evaluated and processed further in various ways.

A first option is to normalize it with the aid, for example, of the sigmoid function. This option is shown by the mark B in FIG. 3*b*, which branches to the input of the method step S3 in FIG. 3*a*. It is then possible to carry out not only the method step S3, but then also all the further method steps S4 to S8, as described above with reference to FIG. 3*a*.

Figure 3C:
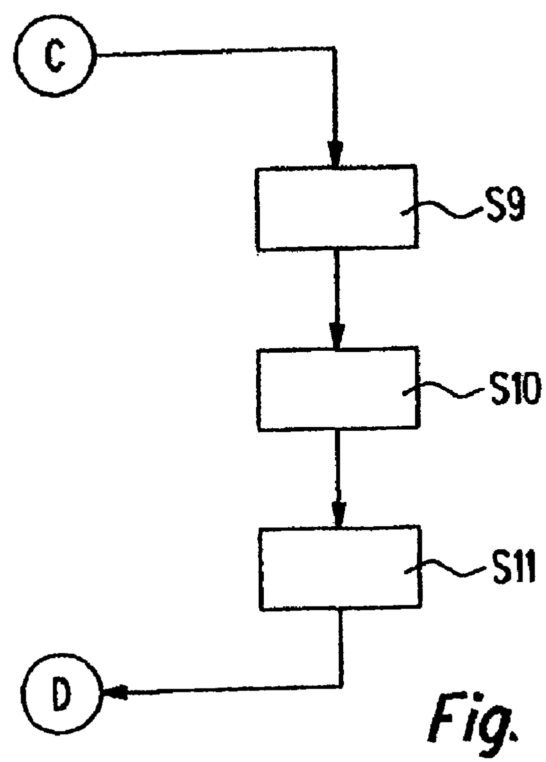

A second option for further processing of the logical operation result obtained in the method step S4/2 once again comprises the normalization process with the aid of the sigmoid function in method step S3; but the evaluation process does not then continue further in accordance with method step S4 and so on. Rather, as is indicated by the mark C in FIG. 3*a*, the further processing continues in method step S9, as shown in FIG. 3*c*. This step indicates that the calculation of the logical operation result which has already been carried out (irrespective of whether it was in accordance with the first exemplary embodiment in step 2 or the second exemplary embodiment in step S4/2), should be carried out more than once during a predetermined measurement time interval. The repeated calculation of the logical operation results at different times ti where i=1–I throughout the measurement time interval provides a large number of logical operation results, preferably at the end of the measurement time interval. As already described, these logical operation results are preferably tapped off at the output of the method step S3, because they are then in a normalized form. However, alternatively, the logical operation results which have been obtained directly in the method steps S2 and S4/2 can also be collected and stored directly in method step S9. These logical operation results are then individually weighted in the method step S10, by allocating a weighting factor to each of these results. These weighting factors represent the respective driving situation of the vehicle or the current distraction of the driver, in each case at a time to which the logical operation result relates.

Then, finally, a weighted logical operation result is calculated in the method step S11 by mathematical, preferably arithmetic, weighted averaging of the logical operation results obtained during the measurement time interval, taking into account the weighting factors associated with them.

The weighting factors are defined taking into account the time of day, (that is, circadian influencing factors and/or the time since the start of the journey). The weighted result of the logical operation provides a very reliable measure of driver inattentiveness which, in particular, is relatively simple and fast. This averaged result of the logical operation is then preferably subjected to an error criterion, as in FIG. 3*c* in conjunction with FIG. 3*a* via the mark D in the method step S8, and is evaluated in order to generate a warning signal for the driver. The error criterion is satisfied when the sum of all of the logical operation results calculated in the most recent x minutes, in each case weighted with their individual weighting factors, exceeds a predetermined threshold value.

The second option, as described above, for further processing of the logical operation result obtained in the method step S4/2 according to the second exemplary embodiment, by means of the steps S9 to S11, is also appropriate, in the same way, for the logical operation result obtained in the method step S2 according to the first exemplary embodiment.

A third option for further processing of the logical operation result from step S2 or from step S4/2 is to preferably carry out the steps S4 to S7 and S9 to S11 in parallel, in time.

The two exemplary embodiments of the method according to the invention, in all of their variants, are preferably implemented in the form of at least one computer program. If required, the computer program may be stored together with further computer programs in a data storage medium, such as a floppy disk, a compact disk, a so-called flash memory or the like. The computer program which is stored in the data storage medium can then be sold as a product to a customer. As an alternative to transferring it in the form of a data storage medium, it is also possible to transmit it via a communications network, in particular the Internet.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed:

1. A method for determining when a driver of a vehicle is inattentive, said method comprising:

detecting movement of a steering wheel of the vehicle in the form of a steering wheel angle x;

detecting occurrence of a steering quiescent phase;

determining an extent, in terms of time duration, of the steering quiescent phase, based on at least one of the detected steering wheel angle and a rate of change of said steering wheel angle;

identifying a steering action following the steering quiescent phase;

determining the extent of the steering action by evaluating the rate of change of the steering wheel angle; and determining a measure of severity of driver inattentiveness, based on the result of a link between the extent of the steering quiescent phase and the extent of the steering action; wherein, the extent of the steering quiescent phase is determined as a time period during which the steering wheel angle remains within a predetermined steering wheel angle interval;

the extent of the steering action following a previous steering quiescent phase is determined in the form of the maximum gradient of the steering wheel angle which then occurs;

the link between the extent of the steering quiescent phase and the extent of the steering action at a time t1 is produced by means of a multidimensional operator, only when the extent of the steering quiescent phase is greater than a predetermined minimum time and the maximum gradient of the steering wheel angle exceeds a predetermined gradient threshold value;

a steering wheel angle interval is predetermined on the basis of the current speed of the vehicle;

the multidimensional operator represents one of a family of characteristics, a weighting function and a logical decision function;

the multidimensional operator is dimensioned based on at least one of the speed of the vehicle, and dynamics of a driving style of the driver of the vehicle;

in a subsequent step a result of the logical operation is mapped in the form of the multidimensional operator onto a probability value $P(U_1)$ between 0 and 100%, which represents the inattentiveness by the driver in the steering of the vehicle at the time $t_1$; and the method further comprises, determining a first probability vector $O_{n=1}$, whose elements $O_{n=1,k1}$ each represent probability values $P(O_{1,k1})$, of a probability value $P(U_1)$ occurring in individual, predetermined and selected extent levels $k_1$ where $k_1 \in \{1 \ldots K_1\}$; and determining a fatigue probability vector S', whose elements each represent fatigue level probabilities P that detect driver inattentiveness is associated with individual, predetermined and suitably selected fatigue levels, using the following formula:

$$S'(t)O_1^T \cdot B_1; \quad (5),$$

with $O^T_1$ representing the transpose of the first probability vector;

$B_1$ the matrix B representing predetermined conditional probabilities with respect to the steering inattentiveness, represented by the indicator n=1; and $K_1$ representing the number of extent levels for the indicator n=1.

2. The method according to claim 1, wherein said mapping is performed based on a sigmoid function.

3. The method according to claim 1, further comprising the following further steps:

determining further probability vectors On=2 . . . $O_{n=N}$ whose elements $O_{n,kn}$ were k=1 . . . $K_n$ each represent probabilities $P(O_{n,kn})$ of the probability values $P(U_n)$ occurring for inattentiveness indicators n=2 . . . N other than steering inattentiveness n=1, in individual predetermined extent levels $k_n$; and calculating the fatigue probability vector S" in the method step S6 using the following formula (6):

$$S''(t) = \prod_{n=1}^{N} O_n^T \cdot B_n, \quad (6)$$

where

N represents the n-th indicator for the inattentiveness by the driver;

$O_n^T$ represents the transpose of the further probability vectors;

$B_n$ represents the matrix B for the indicator n; and

N represents the number of indicators.

4. The method according to claim 3, wherein said inattentiveness indicators n include at least one of eyelid closure behavior and reaction time.

5. The method according to claim 4, further comprising:

storing the fatigue probability vector S'"(t−1); and calculating a more precise fatigue probability vector S'"(t) using the following formula (7) (method step S7):

$$S'''(t)=S''(t)\cdot A\cdot S'''(t-1), \quad (7)$$

where

A represents the matrix of the conditional probabilities between a fatigue level from the last time step and a current fatigue level.

6. The method according to claim 5, wherein:

in addition to steering inattentiveness and optional further indicators for driver inattentiveness, the method further determines further events, including whether the driver is holding a conversation or is using a control element; and the further events are evaluated based on the probabilistic model, in order to determine the probability with which it can be assumed that the driver has been distracted by such further events, and the probability of driver fatigue being the cause of the observed inattentiveness.

7. The method according to claim 6, wherein said further events include at least one of operation of a radio or glove compartment.

8. A method for determining when a driver of a vehicle is inattentive, said method comprising:

detecting movement of a steering wheel of the vehicle in the form of a steering wheel angle;

detecting occurrence of a steering quiescent phase, being a phase during which the steering wheel angle remains within a steering wheel angle interval that is determined based on a current speed of the vehicle;

determining an extent, in terms of time duration of the steering quiescent phase based on at least one of the detected steering wheel angle and a rate of change of said steering wheel angle;

identifying a steering action following the steering quiescent phase;

determining an extent of the steering action by evaluating a rate of change of the steering wheel angle; and determining inattentiveness of the driver only if the steering quiescent phase and a following steering action of a preset magnitude are identified in conjunction with one another.

9. The method according to claim 8, wherein the step of determining the extent of the steering action is based on a maximum detected gradient of the steering wheel angle.

10. The method according to claim 9, where the act of determining inattentiveness of the driver is performed only when the extent of the steering quiescent phase is greater than a predetermined minimum time period and a maximum gradient of the steering wheel angle exceeds a predetermined gradient threshold value.

11. The method according to claim 8, further comprising the act of:

determining a measure of severity of the inattentiveness by the driver while steering the vehicle, by assessing a result of a link between the extent of the steering quiescent phase and an extent of the steering action.

12. The method according to claim 11, further comprising the act of producing the link at a time ti between the extent of the steering quiescent phase and the extent of the steering action by use of a multidimensional operator, wherein the multidimensional operator comprises at least one from the group of a family of characteristics, a weighting function and a logical decision function.

13. The method according to claim 12, further comprising the act of dimensioning the multidimensional operator based on at least one of vehicle speed and dynamics of a driving style of the driver.

14. The method according to claim 12, further comprising:

processing a logical operation result in the form of the multidimensional operator using a sigmoid function to give a probability value between 0 and 100 percent as a probability of inattentiveness by the driver in steering the vehicle at time $t_1$.

15. The method according to claim 14, further comprising the following acts for assessing fatigue of the driver:

determining a first probability vector $O_{n=1}$, whose elements $O_{n=1,k1}$ each represent probability values $P(O_{1,k1})$, of a probability value $P(U_1)$ occurring in individual, predetermined and selected extent levels $k_1$ where $k_1 \in \{1 \ldots K_1\}$; and determining a first fatigue probability vector S', whose elements each represent fatigue level probabilities P that a detected driver inattentiveness is associated with individual, predetermined and suitably selected fatigue levels, using the formula:

$$S'(t)=O_1^T B_1;$$

where $O_1^T$ represents the transpose of a first probability vector;

$B_1$ represents the matrix B representing predetermined conditional probabilities with respect to a steering inattentiveness, represented by the indicator n=1; and $K_1$ represents the number of extent levels for the indicator n=1.

16. The method according to claim 15, further comprising the acts of:

determining further probability vectors $O_{n=2} \ldots O_{n=N}$ whose elements $O_{n,kn}$, where $k_n=1 \ldots K_n$, each represent probabilities $P(O_{n,kn})$ of the probability values $P(U_n)$ occurring for other inattentiveness indicators n=2 . . . N, in addition to the steering inattentiveness n=1, in individual predetermined extent levels $k_n$; and calculating a second fatigue probability vector S" using the formula:

$$S''(t) = \prod_{n=1}^{N} O_n^T \cdot B_n$$

where n represents the n-th indicator for the inattentiveness by the driver;

$O^T_n$ represents the transpose of the further probability vectors;

$B_n$ represents the matrix B for the indicator n; and

N represents the number of indicators.

17. The method according to claim 15, further comprising:

storing a third fatigue probability vector in the time period $t_1-1$, S''' $(t_1-1)$; and calculating a more precise fatigue probability vector S'''(t) using the formula:

$$S'''(t)=S''(t)\cdot A\cdot S'''(t_1-1)$$

where A represents the matrix of the conditional probabilities between a fatigue level in a most recent time interval and a current fatigue level.

18. The method according to claim 17, wherein:

in addition to steering inattentiveness and other inattentiveness, the method also determines further events, including whether the driver is holding a conversation or is using a control element; and the further events are evaluated based on a probabilistic model in order to determine a probability with which it can be assumed that the driver has been distracted by said further events and a probability of driver fatigue being the cause of the inattentiveness.

19. The method according to claim 11, wherein:

a logical operation is carried out at different times ti where i=1-I during a predetermined measurement time interval;

results of a plurality of logical operations relating to a corresponding plurality of times ti are, in each case, stored together with respective associated weighting factors which represent at least one of a driving situation of the vehicle and a current distraction of the driver, in each case relating to the time ti; and a weighted result of the logical operation is calculated by an averaging of the results stored during the predetermined measurement time interval, taking into account the weighting factors associated with said results.

20. The method according to claim 19, wherein the weighting factors are calculated taking into account at least one of circadian influencing factors and time elapsed since a journey started.

21. The method according to claim 19, further comprising an outputting of information when a weighted result exceeds a predetermined threshold value.

22. A computer readable data storage medium included with a program for determining when a driver of a vehicle is inattentive, said program including means for:

detecting movement of a steering wheel of the vehicle in the form of a steering wheel angle, wherein a steering wheel angle interval is predetermined based on a current speed of the vehicle;

detecting occurrence of a steering quiescent phase;

determining an extent, in terms of time duration, of the steering quiescent phase based on at least one of the detected steering wheel angle and a rate of change of said steering wheel angle, wherein the extent of the steering quiescent phase is determined as that time period during which the steering wheel angle remains within the predetermined steering wheel angle interval;

identifying a steering action following the steering quiescent phase;

determining an extent of the steering action by evaluating a rate of change of the steering wheel angle, and determining inattentiveness of the driver only if the steering quiescent phase and the following steering action are identified in conjunction with one another.

23. A computer program with program code for a controller for identification of inattentiveness by a driver of a vehicle, wherein the program code includes steps to carry out the method according to claim 8.

24. The method according to claim 16, wherein said other inattentiveness indicators include at least one of eyelid closure behavior and reaction time.

* * * * *